United States Patent [19]

Colegate et al.

[11] 4,033,764

[45] July 5, 1977

[54] RECOVERY OF METALS

[75] Inventors: Terence Dudley Colegate, Copthorne; Christopher Robert Farnworth, Thornton Heath; Eric Joseph Davis, Birmingham, all of England

[73] Assignee: Laporte Industries Limited, London, England

[22] Filed: May 20, 1975

[21] Appl. No.: 579,295

[30] Foreign Application Priority Data

May 21, 1974 United Kingdom ............ 22640/74

[52] U.S. Cl. .................................. 423/24; 75/117; 75/119; 75/120; 75/121; 252/455 Z; 210/24; 423/54; 423/63; 423/70; 423/100; 423/112; 423/139

[51] Int. Cl.$^2$ ................. C22B 43/00; C22B 15/00; C22B 26/00

[58] Field of Search ............. 75/101 BE, 121, 118, 75/117, 119; 252/455 Z; 210/24; 423/24, 54, 63, 70, 100, 112, 139

[56] References Cited

UNITED STATES PATENTS

| | | | |
|---|---|---|---|
| 3,200,082 | 8/1965 | Breck et al. | 252/455 Z |
| 3,699,207 | 10/1972 | Roever et al. | 423/100 |
| 3,849,533 | 11/1974 | Hetz | 423/99 |
| 3,872,001 | 3/1975 | Davis et al. | 210/58 |

FOREIGN PATENTS OR APPLICATIONS

| | | | |
|---|---|---|---|
| 592,862 | 2/1960 | Canada | 75/101 BE |
| 1,336,241 | 11/1973 | United Kingdom | 75/101 BE |
| 831,745 | 3/1960 | United Kingdom | 75/101 BE |

OTHER PUBLICATIONS

Kirk–Othmer, Encyclopedia of Chemical Technology, 2nd Edn., vol. 5, Interscience Publishers, N. Y., 1963, pp. 541–557.

*Primary Examiner*—G. Ozaki
*Attorney, Agent, or Firm*—Larson, Taylor and Hinds

[57] ABSTRACT

Metal ions may be scavenged from solution by means of a complexing agent comprising an inorganic substrate, such as a clay mineral, with covalent organic molecules, such as onium compounds, chemically bonded to the substrate, the covalent organic molecules containing free coordinating groups. The complexing agents are particularly useful in scavenging environmentally harmful metal ions such as mercury from industrial effluents.

16 Claims, No Drawings

RECOVERY OF METALS

This invention relates to the removing of metal ions from solution by means of complexing agents.

Complexing agents have been proposed for use in combination with adsorbents to recover metal ions from solution. British Pat. No. 1,355,535 discloses the use of an adsorbent comprising peat, brown coal or a 'char', derived by heating brown coal, in combination with ammonia or an organic derivative thereof, capable of forming a complex with the dissolved metal, for this purpose. British Pat. No. 1,336,241 discloses the use of a chelating agent containing a —OH group and one or more groups selected from —N= and —NH$_2$ groups adsorbed onto a carrier, which is preferably active carbon, to recover dissolved metals. British Pat. No. 831,745 discloses the use of a water insoluble chelating agent adsorbed onto an adsorbent which may be a resin or an adsorbent char. Such previous proposals are subject to the disadvantage of a relatively weak connection between the complexing agent and the adsorbent giving rise to the possibility of loss of complexing agent and where the complexing agent is water-soluble this loss may be considerable.

According to one aspect thereof the present invention provides a process for removing metal ions from solution comprising contacting the solution with a complexing agent comprising an inorganic substrate and covalent organic molecules chemically bonded to the substrate, the organic molecules containing free coordinating groups. The invention also provides a new composition useful as a source of metal ions comprising the said complexing agent bearing metal ions complexed thereto. In a liquid medium the metal ions are given off slowly and progressively. Where the metal ions are toxic the composition may find use as a pesticide or herbicide. Preferably the chemical bonding is ionic. Preferably the majority of the covalent organic molecules are ionically bonded to the substrate.

The inorganic substrate is insoluble in water and must be suitable for bonding the covalent organic molecules thereto.

Very suitably the substrate may have a layered structure based on silicon or phosphorus atoms and preferably is provided by a clay mineral having a layered structure based on silicon atoms. Suitable clay minerals may belong to any of the groups of minerals described in Kirk-Othmer, Encyclopaedia of Chemical Technology, 2nd Edition (1963), Volume 5, pages 541–557. Preferably the substrate is a member of the smectite group which have structures based on that of the mineral pyrophillite, which consists of superimposed layers each of which contains a plane of Al '3$^+$ ions sandwiched between two inward pointing sheets of linked SiO$_4$ tetrahedra. The central Al$^{3+}$ section may be regarded as a layer of gibbsite Al$_2$ $_{(OH)6}$ in which 2 out of 3 OH ions are replaced by apical oxygens of an Si$_4$O$_{10}$ pseudo-hexagonal network. The charge balance is upset by substitution in both octahedral (Al) and tetrahedral (Si) sites and is redressed by a small number of inter-layer cations usually sodium or calcium cations. The smectite group of minerals have a chemical formula analogous to those of either pyrophyllite or talc but in which substitutions in octahedral or tetrahedral sites by ions of lower valency are accompanied by the addition of an equivalent number of inter-layer cations. The average extent of such substitution requires about 0.66 additional monovalent cations per formula unit and these ions are in general exchangeable. The formula of the smectite group may be expressed:

$$(\tfrac{1}{2}Ca,Na)_{0.66}(Al,Mg,Fe)_4(Si,Al)_8O_{20} \quad (OH)_4 nH_2O$$

The smectite group includes the following minerals:

| | | | |
|---|---|---|---|
| Montmorillonite | Si$_8$ | Al$_{3.34}$Mg$_{0.66}$ | ($\tfrac{1}{2}$ Ca,Na)$_{0.66}$ |
| Beidellite | Si$_{7.34}$Al$_{0.66}$ | Al$_4$ | ($\tfrac{1}{2}$ Ca,Na)$_{0.66}$ |
| Nontronite | Si$_{7.34}$Al$_{0.66}$ | Fe$_4^{3+}$ | ($\tfrac{1}{2}$ Ca,Na)$_{0.66}$ |
| Saponite | Si$_{7.34}$Al$_{0.66}$ | Mg$_6$ | ($\tfrac{1}{2}$ Ca,Na)$_{0.66}$ |
| Hectorite | Si$_8$ | Mg$_{5.34}$Li$_{0.66}$ | ($\tfrac{1}{2}$ Ca,Na)$_{0.66}$ |
| Sauconite | Si$_{6.7}$Al$_{1.3}$ | Zn$_{4-5}$(Mg,Al,Fe$^{3+}$)$_{2-1}$ | ($\tfrac{1}{2}$ Ca,Na)$_{0.66}$ |

Many of the bentonite minerals, which are particularly suitable for use in the present invention, have a high cation exchange capacity which makes possible the ionic bonding of a relatively large quantity of covalent organic molecules to it. The majority of the exchangeable cations of the substrate are preferably sodium cations. A particularly suitable clay mineral which is, in its natural state, substantially in the sodium form is Wyoming bentonite. Alternatively a synthetic clay mineral such as that produced by a process described in British Pat. No. 1,054,111 or British Pat. No. 1,213,122 may be used. Alternatively the exchangeable cations of the substrate may be alkaline earth metal cations. Preferably the cation exchange capacity of the substrate is at least 0.5 m.eq/g and, particularly, at least 0.65 m.eq/g.

Onium compounds are particularly suitable for attachment by ion exchange to the anionic framework of clay minerals as above described. The term "onium compound" is used herein to mean nitrogen compounds or isologues thereof based on phosphorus, arsenic, antimony, oxygen, sulphur, selenium or tin groups having the general formula R$_n$ XH$_m^+$ B$^-$ where X is one of the above mentioned elements, R is an organic radical and $n$ and $m$ are numbers, the sum of $n$ and $m$ equalling 4 where the element is nitrogen, phosphorus, arsenic or antimony and equalling 3 where the element is oxygen, sulphur, selenium or tin. B$^-$ is an anion, for example a chloride ion. Particularly suitable onium compounds are those based on nitrogen and which may be prepared by protonating the corresponding amine by means of a strong acid such as hydrochloric acid. Preferably the onium compound is derived from a diamine in which the amine groups have different reactivities with acid and which has been reacted with strong acid in such a manner as to protonate only one of the amine groups. The resulting compound will, after ion exchange onto the substrate, leave a free nitrogen-containing coordinating group.

Suitably the quantity of the onium compound is from 0.9 to 1.3 times and preferably from 1.0 to 1.3 times the cation exchange capacity of the substrate to ensure substantial saturation of the substrate. Adduction is preferably effected in the presence of sufficient water to allow the transfer of the onium cations. It is desirable for as high a proportion as possible of the onium compound to be bonded to the substrate by ion exchange and it follows then the conditions used to perform the adduction should be controlled with this factor in mind. The substrate is preferably treated in the form of a dispersion in water at a concentration of, for example, from 1 to 12% by weight. It is an important factor in achieving an efficient adduction that the substrate be in a highly dispersed state. The presence of shear assists dispersion and a suitable way of attaining this is by agitating a suspension of the substrate by means of a high shear stirrer. Additionally a dispersion agent, such as tetrasodium pyrophosphate, may be included in the suspension. The quantity of dispersing agent may be suitably in the range of 0.1% to 5% and preferably from 1% to 4% by weight of the substrate. If any aggregates of substrate remain undispersed it may be desirable to remove such aggregates for example by centrifuging. The onium compound may be added to the suspension of the substrate or may itself be dispersed in water, for example at a concentration of from 1% to 6% by weight, and the two dispersions then mixed by slowly adding the suspension of the onium compound to the dispersion of the substrate. Preferably the dispersion of the substrate and the mixed dispersions are maintained under shear throughout and for a sufficient time after mixing has been completed to allow the adduction to go to completion, for example, for up to 30 minutes after mixing has been completed. Preferably the temperature is maintained throughout at from 10° C to 90° C depending on the thermal stability of the organic compound.

The derivative resulting from the adduction may be filtered and washed free of inorganic cations from the substrate and anions from the onium compound. The derivative is then preferably dried to a water content of from 1% to 3%. Depending on the onium compound used it may be necessary to control the temperature of drying carefully to avoid breakdown of the adduct.

The covalent organic compound may have a chain of more than 10 or even more than 18 carbon atoms. Examples of suitable onium compounds having such chains are those derived from unsymmetrical diamines based on coconut, tallow or soya been oil and available under the Trade Name Duomeen. Alternatively relatively short chain onium compounds may be used. One suitable short chain compound which may be converted into an onium compound is diethylene triamine. The primary and secondary amine groups of diethylene triamine protonate differentially making possible the retention of nitrogen containing groups capable for complex formation with metals in the final adduct.

It is a particular advantage of the invention that water soluble complexing agents such as diethylene triamine or cysteine may be rendered insoluble by incorporation with an inorganic substrate according to this invention thus avoiding losses of complexing agent inherent in prior processes relying on the use merely of an adsorbent as a substrate. The metals to be recovered are firmly bound through the complexing agent to the substrate and are thus easily and quantitatively removable from solution.

The coordinating groups carried on the covalent organic molecule may be any known to give usefully stable complexes. It is possible to grade the complex stability of coordinating ions or molecules into a series. To be effective in coordinating suitable metals in aqueous systems the organic molecule attached to the substrate should bear a coordinating group or combination of groups giving a greater complex stability than water. The preferred coordinating groups are: $-NH_2$, $>NH$, $-COOH$, $-OH$ or

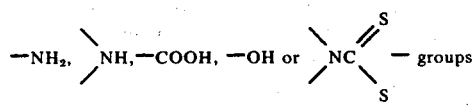 groups or combinations of these with each other or with other coordinating groups. Where such groups act together to form a ring with the metal, for example a five or six membered ring, a chelate complex of considerable stability is formed and a such complex may be useful in the present invention.

The coordinating groups may be introduced into the covalent organic compound after it has been adducted onto the substrate or alternatively a suitable compound already containing a coordinating group may be adducted, onto the substrate, as such.

Certain metals are known to form more stable complexes with certain types of ligand than with others. It is desirable therefore to bear this factor in mind when selecting a ligand. Some metals form more stable complexes with S donor ligands or O donor ligands than with the N donor ligands which have been described above. A suitable S donor ligand may be obtained by reacting a primary amine group with carbon disulphide in the presence of ethanol to form a dithiocarbamic acid group. By this route an onium compound as described above and containing a free primary amine coordinating group may be treated to convert the previous N donor ligand into an S donor ligand. Examples of O donor ligands are nitrilotriacetic acid and 5-amino-salicylic acid. Both of these compounds may be protonated as above described to form onium compounds suitable for attachment to substrate by ion exchange. The following figure illustrates with reference to the periodic table the tendency of various metals to form stable complexes with particular types of ligand.

| Classification of elements capable of complexing according to preferred donor atoms. | | | | | | | | |
|---|---|---|---|---|---|---|---|---|
| Group 1a | 2a | 3b | 4b | 5b | 6b | 7b | 8 | 8 |
| + Li | + Be | | | | | | | |
| + Na | + Mg | | | | | | | |
| + | + Ca | + Sc | + Ti | + V | + Cr | + Mn | + Fe | Δ Co |
| + Sr | + Y | + Zr | + Nb | + Mo | + Tc | ++ Ru | Δ++ Rh | |
| + Ba | + La | + Hf | + Ta | + W | + Re | ++ Os | Δ++ Ir | |
| Lanthanides | + Ce | + Pr | + Nd | + Pm | + Sm | + Eu | + Gd | |
| Actinides | + Th | + Pa | + U | + Np | Pu | Am | Cm | |

+ Oxygen donor
++ halogen, sulphur oxygen or carbon donor
Δ nitrogen donor
* sulphur donor

| Classification of elements capable of complexing according to preferred donor atoms. | | | | | | | | |
|---|---|---|---|---|---|---|---|---|
| Group 8 | 1b | 2b | 3a | 4a | 5a | 6a | 7a | 0 |
| | | | + Al | | | | | |
| Δ++ Ni | Δ++ Cu | Δ Zn | + Ga | +* Ge | | | | |
| Δ++ Pd | Δ++ Ag | Δ++ Cd | + In | +* Sn | +* Sb | | | |
| Δ++ Pt | Δ++ Au | Δ++ Hg | ++ Tl | +* Pb | +* Bi | | | |
| + Tb | + Dy | + Ho | + Er | + Tm | + Yb | + Lu | | |
| Bk | Cf | | | | | | | |

Preferably the metal recovered is a transition element selected from groups 1b to 7b inclusive or from group 8 of the periodic table or is a complex forming lanthanide or actinide or is selected from groups 4a and 5a the group identification being that used in the figure.

Some industrial processes result in liquors containing trace quantities of a variety of metals. The electrolytic refining of copper on a commercial scale results in a slime at the bottom of the tank containing gold, silver and lead and the tank liquor contains iron zinc and nickel. Platinum, rhodium, iridium, rhenium, osmium and ruthenium are distributed between the liquor and the slime. The electrolysis of alkali salts in a mercury cell gives rise to waste liquors containing mercury ions which can cause great environmental pollution problems. Many industrial organic synthetic processes which use metals as catalysts may also give rise to waste liquors containing the metals which it may be desired to recover on either environmental or economic grounds. The present invention may be utilised to recover metals from such liquors. The anions present in the liquors are not critical but may commonly be acetate, sulphate, nitrate, chloride, cyanide, formate or chromate anions.

It is envisaged that mixtures of metal ions may be separated by making use of the different tendency to form coordination complexes of different metal ions. If, for example, a solution containing a mixture of transition metal ions is passed through a column of the complexing adduct a separation may occur if the metals have different affinities for the complexing group.

The complexing adduct of the present invention may be used as a bed through which the metal-containing liquid to be treated may be passed. Alternatively, if the complexing agent is slurried in the liquid to be treated, it is readily recoverable by filtration. To render the complexing agent more readily usable, by increasing the permeability of a column thereof, it may be coated onto carrier particles, by, for example, pan pelletisation. Alternatively the complexing agent may be incorporated in a porous polymer matrix through which the liquid to be treated may be percolated. When the complexing adduct is saturated the metal ions may be recovered by treatment with acid, preferably a strong acid, to enable the metal to be removed as a relatively concentrated eluant. Depending on the coordinating groups present in may be necessary to control the acid concentration carefully to prevent destruction of the coordinating groups. For example, dithiocarbamate coordinating groups may be destroyed if subjected to a pH of less than about 2.0. The resulting protonated coordinating groups can be regenerated to their free form by treatment with alkali.

Examples of processes in which the complexing agents may be used are the treatment of water, and of effluents from industrial processes.

A feature of most complexing agents and their use to recover suitable metals is that metals such as sodium, calcium and magnesium are not complexed by most ligands. Such metals are readily recovered by ion exchange and their presence can render ion exchange processes for the recovery of transition elements unsatisfactory.

The invention will now be illustrated by means of the following Examples which relate to the preparation and use of complexing agents according to the invention.

EXAMPLE 1

8.41g Duomeen T paste (89% purity) was mixed with 20.8 ml 1 N HCl and to the mixture was added 181.0g water to give a concentration of Duomeen T of approximately 4% by weight. The resulting mixture was heated to 50° C to dissolve the Duomeen T. Duomeen T would be expected to be protonated at the secondary nitrogen atom preferentially by the above treatment to give an onium compound having the formula:

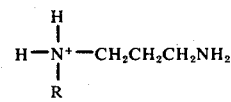

16.0g (dry weight) of Volclay having a cation exchange capacity of 0.8 m.eq/g dry weight was dispersed in 384.0g water by subjecting a mixture to the action of a high shear stirrer for 30 minutes to give a dispersion having a concentration of approximately 4% by weight. Volclay is a Trade Name for a sodium montmorillonite clay. This dispersion was heated to 50° C and the onium compound solution at 50° C was slowly added to it with stirring. The dispersion was allowed to stand for 15 minutes to ensure that the reaction had finished and was filtered and washed free of chloride ion and the filter cake dried in an oven at a temperature no higher than 60° C and ground to pass a 100 BSS sieve. The yield was approximately 90% of theoretical.

The product was the clay having the onium compound chemically attached to it by ion exchange at the onium group and having free primary amine groups.

EXAMPLE 2

The product of Example 1, after drying, was reacted, in ethanol, with a quantity of $CS_2$ in excess of that required stoichiometrically for the reaction.

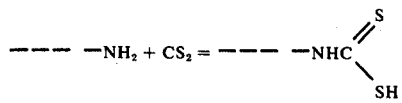

The dithiocarbamate product was washed free of $CS_2$ with methanol and dried.

EXAMPLE 3

500 ml of sea water containing in total 21 micrograms of $Cu^{+2}$ was treated with 1.0g of a complexing agent produced as described in Example 1 and containing 1.3 m.eq of onium compound per g of clay. The complexing agent was dispersed by the use of an ultrasonic vibrator and the dispersion was then left to stand at 25° C for 24 hours. The complexing agent was removed from the sea water by filtration.

The $Cu^{+2}$ content of treated and untreated sea water was measured by atomic absorption spectrophotometry by the following method. This method entailed the use of the following reagents:

1. 20 g sodium diethyldithiocarbamic acid in 380 ml of deionised water,

This was filtered and extracted with two 15 ml portions of methylisobutyl ketone to remove any traces of copper.

2. 102 g of potassium biphthalate dissolved in 500 ml of deionised water, with 14 ml of INHCl added, and diluted to 1 liter.

3. Standards of 1, 5, 10 parts per 1000 million Cu. All samples were filtered through Celite (Trade Mark) and treated as follows:

A 400 ml aliquot of test liquor was measured into a 400 ml flask. 8 ml of phthalate buffer was added and the pH adjusted to 3.6 ± 0.1. After adjustment of the pH, 25 ml of the aqueous thiocarbamate solution was added. The solution was transferred to a 1 liter separating funnel and a 50 ml portion of methylisobutyl ketone was pipetted directly into the funnel. The mixture was shaken vigorously for thirty seconds then allowed to separate for ten minutes. The ketone layer was drawn off into a stoppered Pyrex container and the copper content compared with the standards by atomic absorption spectrophotometry. Pyrex is a Trade Mark.

1.9 micrograms of $Cu^{+2}$ was found to remain in the sea water.

The experiment was repeated using a complexing agent produced as described in Example 2. 1.5 micrograms of $Cu^{+2}$ was found to remain in the sea water.

EXAMPLES 4 – 5

The following complexing agents according to the invention, in which the bonding to the substrate is ionic in nature, were prepared.

4. Sodium Montmorillonite/Duomeen T
5. Sodium Montmorillonite/Duomeen T Dithiocarbamate
6. Sodium Montmorillonite/Diethylene triamine
7. Calcium Montmorillonite/Diethylene triamine
8. Sodium Montmorillonite/5-Amino salicylic acid
9. Sodium Montmorillonite/5-Amino salicylic acid/dodecylamine
10. Sodium Montmorillonite/Aromox DMCDW
11. Sodium Montmorillonite/Aromox C12/W The cation exchange capacity of the clay minerals used was:

Sodium Montmorillonite 0.8 m.eq/dry g.
Calcium montmorillonite 0.69 m.eq/dry g.

4. 5.18 g of Duomeen T paste was mixed with 12.8 ml 1 N HCl and the mixture dissolved in a minimum quantity of distilled water at 50° C to form an onium compound of the following formula:

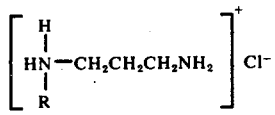

16.0g (dry weight) of a sodium montmorillonite clay available under the Trade Name Volclay and having a cation capacity of 0.8 m.eq/g was dispersed in 384.0g water (4% suspension) by subjecting the mixture to the action of a high shear stirrer for 30 minutes. The dispersion was heated to 50° C and the onium compound solution at 50° C was slowly added to it with constant stirring. Stirring continued for 15 minutes to ensure complete reaction. The Volclay Duomeen T adduct formed by ion exchange at the onium group and having free primary amine groups was filtered off, washed free of chloride ion and dried at 55° C. When dried the adduct was ground to pass a BSS 100 mesh sieve. Final yield was approximately 90% theoretical.

5. The dried product of Example 4 was reacted in ethanol with a quantity of carbon disulphide in excess of the stoichiometric amount needed for the reaction.

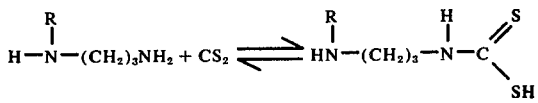

The dithiocarbamate product was washed free of carbon disulphide with methanol and dried.

6. 1.321g of diethylene triamine was mixed with 12.8ml 1 N HCl and the mixture stirred into 400 g of a 4% by weight water suspension of Volclay. The stirring was continued for 15 minutes when the adduct was filtered off and dried at 60° C. When dried the adduct was ground to pass BSS 100 mesh.

7. The preparation was conducted as in Example 6 except that 1.14 g diethylene triamine and 11.0 ml 1 N HCl were used to treat 400 g of a 4% by weight water suspension of calcium montmorillonite available from Laporte Industries Limited as Fullers' Earth No. 1 clay.

8. 2.45g of 5-amino salicylic acid was dissolved in 250 ml of distilled water at 95° C and to this added 16 ml of 1-N HCl acid. The whole was then added to 500g of a 4% by weight suspension of Volclay in water at 95° C. After stirring for 15 minutes the adduct was filtered and washed with hot water. After filtering the adduct was dried at 60° C.

9. 1.21g of 5-amino salicylic acid and 1.48g dodecylamine was mixed with 16.0 ml 1 N HCl. The mixture was heated to about 70° C to dissolve the amines. The method was then the same as Example 8.

10. 13.52g of Aromox DMCDW is a trade name for Dimethylcocoamine oxide (29% purity) was dissolved in 16 ml of 1 N HCl at 50° C, and this mixture added to 500 g of a 4% by weight suspension of Volclay in water also at 50° C. After 15 minutes stirring the adduct was filtered off and dried at 60° C.

11. The preparation was conducted as in Example 6 except that 12.80 g of Aromox C12/W was dissolved in 16 ml of 1 N HCl. Aromox C12/W is a Trade Name for Bis(2-hydroxyethyl)cocoamine oxide.

Removal of metals from solution by means of the products of Examples 4 – 11.

The general technique used was as follows: A weight of adduct, calculated to be sufficient to remove all metal ion present, was stirred with 100 ml of a metal salt solution contained in a 150 ml beaker. Stirring, carried out by a 4 cm stirrer rotating at 100 rpm, was continued for 30 minutes after which time the suspension was filtered through a Whatman No. 3 paper. The filtrate was collected for analysis. The salts used in the experiments were as follows:

Hg, Na, Mn: acetate
Cu, Fe, Cr, Mg, Al: sulphate
Ni, Co, Zn: nitrate
Cd: chloride In some instancrs comparative experiments were conducted using a commercial chelating resin available under the Trade Name Chelex 100 and a commercial cation exchange resin available under the Trade Name Zeokarb 225SRC14 in the sodium form In some instances, where $Cu^{2+}$ or $Hg^{2+}$ were the metal ions being removed, the filter cake was washed with Y mls of acid (see table) followed by Y mls of distilled water to recover the metal from the adduct. When there were no drops of water coming from the cake it was treated with Z mls of ammonium carbonate and Z mls of water. The adduct was then ready for reuse.

| Wt. of clay adduct (g) | Volume (Y) and strength of acid | Volume (Z) and strength of $(NH_4)_2CO_3$ |
|---|---|---|
| 0.25 | 10 mls 0.1N | 4 mls 0.1N |
| 2.5 | 100 mls 0.1N | 40 mls 0.1N |
| 25.0 | 100 mls 1N | 40 mls 1N |

The metal content of the filtrate could then be determined by analysis.

In many instances all or substantially all of the metal removed from solution was accounted for in the filtrate. For example, in Experiments 14 to 16 all of the mercury was accounted for and in Experiments 22, 27 and 29 more than 95% of the copper for accounted for. Thus the present invention may lend itself to cyclic operation with re-use of the adduct after recovery of the metal removed from solution. In the case of Experiments 23 and 27 only 0.1% of the Duomeen T and none of the diethylene triamine was lost from the substrate during contact with the metal solution.

The results obtained in the above described experiments on the removal of mercury, copper and other metals from solution of their salts are set out in the following tables.

| Mercury ($Hg^{2+}$) results | | | | | |
|---|---|---|---|---|---|
| Example | 12 | 13 | 14 | 15 | 16 |
| Adduct of Ex. | 4 | 5 | 6 | 6 | 6 |
| Wt. adduct (g) | 2.5 | 2.5 | 0.25 | 2.5 | 2.5 |
| Hg (initial) ppm | 91 | 91 | 8.4 | 118 | 97 |
| Hg (final) ppm | 0.008 | 0.26 | 0.005 | 0.008 | 0.004 |
| Na (initial) ppm | — | — | 9.2 | — | 101 |
| Na (final) ppm | — | — | 11.5 | — | 105 |

| Example | 17 | 18 | 19 | 20 | 21 |
|---|---|---|---|---|---|
| Adduct of Ex. | 6 | 7 | Chelex | | Zeokarb |
| Wt. adduct (g) | 2.5 | 0.5 | 2.5 | 2.5 | 2.5 |
| Hg (initial) ppm | 91 | 96 | 97 | 118 | 97 |
| Hg (final) ppm | 0.054 | 0.254 | 0.034 | 10.1 | 34.2 |
| Na (initial) ppm | 1185 | — | 1185 | — | 101 |
| Na (final) ppm | 995 | — | 228 | — | 52.5 |

| Copper ($Cu^{2+}$) results | | | | | | | |
|---|---|---|---|---|---|---|---|
| Example | 22 | 23 | 24 | 25 | 26 | 27 | 28 |
| Adduct of Ex. | 4 | 4 | 5 | 6 | 6 | 6 | 6 |
| Wt. adduct (g) | 2.5 | 2.5 | 2.5 | 0.25 | 0.25 | 2.5 | 2.5 |
| Cu (initial) ppm | 38.9 | 101 | 101 | 3.85 | 3.7 | 99 | 370 |
| Cu (final) ppm | 0.4 | 0.95 | 25 | <0.1 | 0.1 | 1.3 | 2.7 |
| Fe (initial) ppm | — | — | — | — | 0.66 | — | — |
| Fe (final) ppm | — | — | — | — | nd | — | — |
| Ni (initial) ppm | 41.9 | — | — | 4.0 | 3.8 | — | 270 |
| Ni (final) ppm | 21.5 | — | — | 0.1 | 0.1 | — | 1.5 |
| nd = none detected | | | | | | | |
| Example | 29 | 30 | 31 | 32 | 33 | 34 | |
| Adduct of Ex. | 7 | 8 | 9 | 10 | 11 | Chelex | |
| Wt. adduct (g) | 0.5 | 2.5 | 2.5 | 2.5 | 2.5 | 2.5 | |
| Cu (initial) ppm | 108 | 115 | 115 | 115 | 115 | 38.9 | |
| Cu (final) ppm | 0.4 | 11.5 | 30.3 | <0.05 | 4.9 | 0.2 | |
| Ni (initial) ppm | — | — | — | — | — | 10 | |
| Ni (final) ppm | — | — | — | — | — | <0.1 | |

| | | | Metals other than Hg and Cu | | |
|---|---|---|---|---|---|
| Ex. No. | Adduct (2.5 g) of Example | Metals | | Concn. (initial) | Concn. (Final) |
| 35 | 3 | $Al^{3+}$ | | 106 | 45 |
| 36 | 3 | $Co^{2+}$ | | 96 | 9.0 |
| 37 | 3 | $Mg^{2+}$ | | 116 | 7.7 |
| 38 | 3 | $Mn^{2+}$ | | 114 | nd |
| 39 | 3 | $Co^{2+}$ | | 3.9 | <0.1 |
| | | $Cr^{3+}$ | | 4.4 | nd |
| | | $Mn^{2+}$ | | 4.6 | 3.1 |
| 40 | 3 | $Co^{2+}$ | | 38 | 0.2 |
| | | $Cr^{3+}$ | | 44 | 1.2 |
| | | $Mn^{2+}$ | | 46 | 32 |
| 41 | 1 | $Mn^{2+}$ | | 46 | 36 |
| | | $Co^{2+}$ | | 38 | 14 |
| | | $Cr^{3+}$ | | 44 | 48 |
| 42 | 3 | $Co^{2+}$ | | 104 | 0.6 |
| | | $Cr^{3+}$ | | 132 | 2.9 |
| | | $Mn^{2+}$ | | 106 | 42 |
| 43 | 3 | $Zn^{2+}$ | | 49.3 | 3.6 |
| | | $Cd^{2+}$ | | 45.5 | 15.0 |
| 44 | 1 | $Zn^{2+}$ | | 49.3 | 12.5 |
| | | $Cd^{2+}$ | | 45.5 | 36.4 |

EXAMPLE 45

An adduct comprising Duomeen T bonded on to Volclay at a level of 0.79 m.eq/g was manufactured by mixing 17.8g Volclay dispersed in 382.2g distilled water with 5.11g Duomeen T dispersed in 94.8g distilled water and 14.2g 1 N HCl. A solution of 3.5g $CuSO_4 5H_2O$ in 85.1g distilled water was contacted with the adduct formed which removed substantially all of the $Cu^{+2}$ ions from the solution. The resulting metal containing composition was washed with distilled water until chloride free, dried at 50° C and ground to pass a 200 mesh (BSS) sieve. 0.2g of the metal-containing composition was placed in a Soxhlet thimble and loosely wedged in the bottom with glass wool. The thimble was immersed in a beaker containing 200 ml distilled water by being mounted coaxially on the end of a vertical stirrer shaft by means of a rubber bung. The stirrer was activated to cause rotation of the thimble. Every 24 hours for 10 days the distilled water was removed, analysed for $Cu^{+2}$ and replaced by fresh distilled water. The analysis figures obtained read as follows:

| Day | 1 | 2 | 3 | 4 | 5 | 6 | 7 | 8 | 9 | 10 |
|---|---|---|---|---|---|---|---|---|---|---|
| $Cu^{+2}$ ppm | 0.59 | 0.66 | 0.44 | 0.59 | 0.38 | 0.28 | 0.57 | 0.52 | 0.38 | 0.42 |

This shows the usefulness of such a composition as a slow-release source of metal ions.

We claim:
1. A process for removing, from solution, ions of metals capable of forming coordination complexes comprising contacting the solution with a complexing agent comprising an inorganic substrate and covalent organic molecules of an onium compound chemically bonded to the substrate, the covalent organic molecules containing free coordinating groups, said inorganic substrate comprising a clay mineral of the smectite group and having a layered anionic lattice based on layers of linked $SiO_4$ tetrahedra.

2. A process as claimed in claim 1 wherein the covalent organic molecules are ionically bonded to the substrate.

3. A process as claimed in claim 1 wherein the substrate comprises a bentonite clay mineral.

4. A process as claimed in claim 3 wherein the substrate comprises calcium or sodium montmorillonite.

5. A process as claimed in claim 1 wherein the substrate has a cation exchange capacity of at least 0.50 m.eq/g.

6. A process as claimed in claim 5 wherein the substrate has a cation exchange capacity of at least 0.65 m.eq/g.

7. A process as claimed in claim 1 wherein the organic molecules comprise onium cations, as defined herein, based on the nitrogen atom.

8. A process as claimed in claim 7 wherein the organic molecules are substantially insoluble in water.

9. A process as claimed in claim 1 wherein the cation exchange capacity of the substrate is saturated by the organic molecules.

10. A process as claimed in claim 9 wherein the organic molecules are such as to impart a hydrophobic character to the substrate.

11. A process as claimed in claim 1 wherein the coordinating groups are such as to give a greater complex stability with the metal ions than would water.

12. A process as claimed in claim 11 wherein the coordinating groups are based on the nitrogen atom and the metal to be recovered is one which will coordinate with a nitrogen ligand.

13. A process as claimed in claim 1 wherein a solution containing metal to be removed, is passed through a bed comprising the complexing agent.

14. A process as claimed in claim 1 wherein particles of the complexing agent are dispersed or slurried in a solution of the metal to be removed and are recovered by filtration.

15. A process as claimed in claim 1 wherein the metal removed from solution is recovered from the complexing agent by treatment with acid.

16. A process as claimed in claim 15 wherein the complexing agent, after reaction with further covalent organic compound, if necessary, is used to remove metals from solution.

* * * * *